US010119151B2

(12) United States Patent
Aten et al.

(10) Patent No.: US 10,119,151 B2
(45) Date of Patent: Nov. 6, 2018

(54) METHODS AND DEVICES FOR CHARGED MOLECULE MANIPULATION

(71) Applicant: Brigham Young University, Provo, UT (US)

(72) Inventors: Quentin T. Aten, Orem, UT (US);
Larry L. Howell, Orem, UT (US);
Brian D. Jensen, Orem, UT (US);
Sandra Burnett, Saratoga Springs, UT (US)

(73) Assignee: Brigham Young University, Provo, UT (US)

( * ) Notice: Subject to any disclaimer, the term of this patent is extended or adjusted under 35 U.S.C. 154(b) by 28 days.

(21) Appl. No.: 14/103,618

(22) Filed: Dec. 11, 2013

(65) Prior Publication Data
US 2014/0227785 A1 Aug. 14, 2014

Related U.S. Application Data

(63) Continuation of application No. 12/668,369, filed as application No. PCT/US2008/069550 on Jul. 9, 2008.

(60) Provisional application No. 60/958,624, filed on Jul. 9, 2007.

(51) Int. Cl.
*C12N 15/89* (2006.01)
*C12M 1/42* (2006.01)

(52) U.S. Cl.
CPC ............. *C12N 15/89* (2013.01); *C12M 35/02* (2013.01)

(58) Field of Classification Search
CPC ............................. C12M 35/02; C12N 15/89

USPC ............................................. 435/285.2, 455
See application file for complete search history.

(56) References Cited

U.S. PATENT DOCUMENTS

| | | | |
|---|---|---|---|
| 4,907,258 | A | 3/1990 | Kettler et al. |
| 5,302,523 | A | 4/1994 | Coffee et al. |
| 5,457,041 | A | 10/1995 | Ginaven |
| 6,063,629 | A | 5/2000 | Knoblauch |

(Continued)

FOREIGN PATENT DOCUMENTS

| | | |
|---|---|---|
| JP | H06343478 A | 12/1994 |
| JP | 2003/088383 | 3/2003 |

(Continued)

OTHER PUBLICATIONS

PCT Application PCT/US2008/069550; filed Jul. 9, 2008; Brigham Young University; International Search Report dated Jan. 14, 2009.

(Continued)

*Primary Examiner* — Michael L Hobbs
*Assistant Examiner* — Liban M Hassan
(74) *Attorney, Agent, or Firm* — Thorpe North & Western, LLP (57) ABSTRACT

Systems and methods for manipulating molecular material are provided. In one aspect, for example, a method for manipulating molecular material may include positioning an uncharged needle structure in electrical proximity with a charged molecular material at a first locus in a liquid environment, charging the needle structure such that at least a portion of the charged molecular material becomes associated with the needle structure, moving the needle structure and the first locus relative to one another, and discharging the needle structure to disassociate the charged molecular material at a second locus.

7 Claims, 5 Drawing Sheets

(56) References Cited

U.S. PATENT DOCUMENTS

| | | |
|---|---|---|
| 6,537,800 B1 | 3/2003 | Karube et al. |
| 6,645,757 B1 * | 11/2003 | Okandan et al. .......... 435/285.1 |
| 6,962,782 B1 | 11/2005 | Livache et al. |
| 2002/0061589 A1 * | 5/2002 | King et al. .................... 435/446 |
| 2003/0228695 A1 | 12/2003 | Nakamura et al. |
| 2004/0063100 A1 | 4/2004 | Wang |
| 2006/0052751 A1 | 3/2006 | Eskandari et al. |
| 2007/0087436 A1 | 4/2007 | Miyawaki et al. |
| 2007/0142781 A1 | 6/2007 | Sayre |
| 2008/0124787 A1 | 5/2008 | Christmann |
| 2008/0199399 A1 | 8/2008 | Chen et al. |
| 2009/0130743 A1 | 5/2009 | Miyawaki et al. |
| 2009/0291502 A1 | 11/2009 | Tateyama |
| 2010/0250006 A1 | 9/2010 | Sasaki et al. |

FOREIGN PATENT DOCUMENTS

| | | |
|---|---|---|
| JP | 2003125750 | 5/2003 |
| WO | WO 03/076951 | 9/2003 |
| WO | WO 2004/092369 A1 | 10/2004 |
| WO | WO 2009/009610 A3 | 1/2009 |

OTHER PUBLICATIONS

EP Application EP08796124; filed Jul. 9, 2008; Brigham Young University; Supplementary European Search Report dated Nov. 20, 2013.

* cited by examiner

METHODS AND DEVICES FOR CHARGED MOLECULE MANIPULATION

PRIORITY DATA

This application is a continuation of U.S. patent application Ser. No. 12/668,369, filed on Jan. 8, 2010, which is a U.S. nationalization of PCT Application No. PCT/US08/69550 filed on Jul. 9, 2008, which claims the benefit of U.S. Provisional Patent Application Ser. No. 60/958,624, filed on Jul. 9, 2007, all of which are incorporated herein by reference in their entireties.

GOVERNMENT LICENSE RIGHTS

This invention was made with government support under contract 0428532 awarded by the National Science Foundation. The government has certain rights in the invention.

FIELD OF THE INVENTION

The present invention relates to the micromanipulation of charged molecules. Accordingly, this invention involves the fields of biotechnology, chemistry, and micromanipulation.

BACKGROUND OF THE INVENTION

Microinjection of foreign materials is often problematic, particularly if such microinjection is being performed on a biological structure such as a living cell. Various transfection techniques include the microinjection of foreign genetic material such as DNA into the nucleus of a cell to facilitate the expression of foreign DNA. For example, when a fertilized oocyte (egg) is transfected, cells arising from that oocyte will carry the foreign genetic material. Thus in one application organisms can be produced that exhibit additional, enhanced, or repressed genetic traits. As one example, researchers have used microinjections to create strains of mice that carry a foreign genetic construct causing macrophages to auto-fluoresce and undergo cell death when exposed to a certain drugs. Such transgenic mice have since played roles in investigations of macrophage activity during immune responses and macrophage activity during tumor growth.

Prior art microinjectors function in a similar manner to macro-scale syringes: a pressure differential forces a liquid through a needle and into the cell. In some cases a glass needle that has been fire drawn from a capillary tube can be used to pierce the cellular and nuclear membranes of an oocyte. Precise pumps then cause the expulsion of minute amounts of genetic material from the needle and into the nucleus.

Recently, researchers have produced fine microinjection needles from silicon nitride and silica glass that are smaller than fire drawn capillaries. These finer needles, however, still employ macro-scale pumps similar to those used in traditional microinjectors.

SUMMARY OF THE INVENTION

Accordingly, the present invention provides systems and methods for manipulating molecular material. In one aspect, for example, a method for manipulating molecular material may include positioning an uncharged needle structure in electrical proximity with a charged molecular material at a first locus in a liquid environment, charging the needle structure such that at least a portion of the charged molecular material becomes associated with the needle structure, moving the needle structure and the first locus relative to one another, and discharging the needle structure to disassociate the charged molecular material at a second locus. It should be noted that discharging the needle structure can occur in a variety of ways. For example, in one aspect the needle structure can be discharged to a degree sufficient to release the associated charged molecular material. In another aspect, discharging the needle structure can include reversing the polarity of the needle structure charge to drive the charged molecular material away from the needle structure.

A variety of charged molecular materials are contemplated that can be manipulated according to aspects of the present invention. Non-limiting examples can include DNA, RNA, peptides, polymers, organic molecules, inorganic molecules, ions, and combinations thereof. In one specific aspect of the present invention, the charged molecular material can include DNA, RNA, peptides, and combinations thereof. In another specific aspect, the charged molecular material can include DNA.

Furthermore, numerous first and second loci are contemplated, and the nature and extent of manipulation of molecular material can vary depending on the environment and intended use of the techniques of the present invention. In one aspect, for example, the second locus can be located within a single cell. In another aspect, the second locus can be located within a cell nucleus of the single cell. In yet another aspect, the first locus can be located outside of the single cell.

Additionally, the movement of the needle structure and the first locus relative to one another can vary depending on the relative locations of the first and second loci and the nature and configuration of the movement apparatus. In one aspect, for example, moving the needle structure and the first locus relative to one another comprises moving the needle structure from the first locus to the second locus. In another aspect, the needle structure includes an elongate axis and a loci axis is defined between the first locus and the second locus. As the needle structure and the first locus are moved relative to one another, an angular relationship between the elongate axis and the loci axis remains constant.

The present invention also provides systems for manipulating molecular material. In one aspect, for example, a system for manipulating molecular material can include a needle structure, a charging system electrically coupled to the needle structure, the charging system being operable to charge and discharge the needle structure, and a movement system operable to move the needle structure from a first locus to a second locus. In one specific aspect, the system can further include a charged molecular material sample associated with the needle structure. In another specific aspect, the system can further include a single cell positioned to receive the needle structure upon operation of the movement system. In one aspect the single cell can be an oocyte.

In another aspect, a system for manipulating molecular material can include a moveable support frame and a needle structure associated with the moveable support frame, where the needle structure is operable to carry molecular material therewith. Furthermore, the moveable support frame is operable to moving the needle structure from an initial position to an extended position, where an elongate axis of the needle structure is maintained in a substantially constant orientation as the moveable support frame moves the needle structure from the initial position to the extended position. In one specific aspect, the vertical elevation of the needle structure in the extended position is different from a vertical elevation of the needle structure in the initial position. In another specific aspect, the system can include a charging system electrically coupled to the needle structure, where the charging system is operable to charge and discharge the needle structure. In yet another aspect, the system can include a support structure positioned adjacent to the moveable support frame, where the support structure is operable to secure a single cell in a position to receive the needle structure when in the extended position.

In another aspect, a system for manipulating molecular material can include a moveable support frame, and a needle structure associated with the moveable support frame, where the needle structure is chargeable between a first charged state and a second charged state. Furthermore, the moveable support frame is operable to moving the needle structure from an initial position to an extended position, wherein an elongate axis of the needle structure is maintained in a substantially constant orientation as the moveable support frame moves the needle structure from the initial position to the extended position. In one specific aspect, the vertical elevation of the needle structure in the extended position is different from a vertical elevation of the needle structure in the initial position.

DEFINITIONS OF KEY TERMS

In describing and claiming the present invention, the following terminology will be used in accordance with the definitions set forth below.

The singular forms "a," "an," and, "the" include plural referents unless the context clearly dictates otherwise. Thus, for example, reference to "a support" includes reference to one or more of such supports, and reference to "an oocyte" includes reference to one or more of such oocytes.

As used herein, the term "charged molecular material" may be used to refer to any molecular material that is capable of being attracted to or associated with an electrically charged structure. Accordingly, charged molecular material may be used to refer to those molecules having a net charge, as well as those molecules that have a net neutral charge but possess a charge distribution that allows attraction to the structure.

As used herein, the term "peptide" may be used to refer to a natural or synthetic molecule comprising two or more amino acids linked by the carboxyl group of one amino acid to the alpha amino group of another. A peptide of the present invention is not limited by length, and thus "peptide" can include polypeptides and proteins.

As used herein, the term "uncharged" when used in reference to a needle structure may be used to refer to the relative level of charge in the needle structure as compared to a charged molecular material. In other words, a needle structure may be considered to be "uncharged" as long as the amount of charge on the needle structure is insufficient to attract a useable portion of the charged molecular material. Naturally what is a useable portion may vary depending on the intended use of the molecular material, and it should be understood that one of ordinary skill in the art would be aware of what a useable portion is given such an intended use. Additionally it should be noted that a needle structure with no measurable charge would be considered "uncharged" according to the present definition.

As used herein, the term "sample" when used in reference to a sample of a molecular material may be used to refer to a portion of molecular material that has been purposefully attracted to or associated with the needle structure. For example, a sample of a molecular material such as DNA that is described as being associated with a needle structure would include DNA that has been purposefully attracted thereto, but would not include DNA that is attracted thereto through the mere exposure of the needle structure to the environment. One example of DNA that would not be considered to be a "sample" includes airborne DNA fragments that may associate with the needle structure following exposure to the air.

As used herein, "adjacent" refers to near or close sufficient to achieve a desired effect.

As used herein, "associate" is used to describe molecular material that is in electrostatic contact with a structure due to attraction of opposite charges. For example, DNA that has been attracted to a structure by a positive charge is said to be associated with the structure.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint without affecting the desired result.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore,

DETAILED DESCRIPTION

Aspects of the present invention provide methods and systems for manipulating molecular material. Such methods and systems can include the actual manipulation of the molecular material as well as the movement and positioning of a device or devices used for the manipulation.

It has thus now been discovered that molecular material may be manipulated through the use of a needle structure without the use of a pump mechanism. Such a "pump-less" needle structure utilizes electrical charge to associate and release charged molecular material therefrom. For example, in one aspect a method for manipulating molecular material can include positioning an uncharged needle structure in electrical proximity with a charged molecular material at a first locus in a liquid environment, charging the needle structure such that at least a portion of the charged molecular material becomes associated with the needle structure, moving the needle structure and the first locus relative to one another, and discharging the needle structure to disassociate the charged molecular material at a second locus. Such a method utilizes the charge of a molecular material to facilitate the transfer from the first locus to the second locus. In the case of DNA, for example, such a transfer is made feasible by the unequal charge distributions within DNA molecules. More specifically, the phosphate backbone of DNA has a net charge of one electron per phosphate, giving a total of two electrons per base pair. This net negative charge on the outer backbone of the DNA molecule makes it possible to move DNA from the first locus to the second locus using a charged needle structure.

As further description, an electrical charge is introduced into the needle structure to attract the charged molecular material onto its outer surface. The needle structure can then be moved from the first locus to the second locus along with the associated molecular material. It should be noted that such movement may include moving the needle structure to the second locus, moving the second locus to the needle structure, or a combination of both. Moving to the second locus may also include moving from the outside of a cell to the inside of the cell, moving from one portion of a liquid to another portion of the same liquid, moving from one liquid to another liquid, and the like. Following arrival at the second locus, the molecular material can then be released from the surface of the needle structure. In one aspect, such release may be accomplished by releasing the charge of the needle structure and allowing the molecular material to diffuse away from the structure. In another aspect, the polarity of the charge of the needle may be reversed to electrostatically repel the molecular material from the needle's outer surface at the second locus.

Numerous types of charged molecular material are contemplated for use according to aspects of the present invention, all of which would be considered to be within the present scope. Non-limiting examples include DNA, RNA, peptides, polymers, organic molecules, inorganic molecules, ions, and combinations thereof. In one specific aspect, DNA may be any form of natural or synthetic DNA, including genomic DNA, cDNA, plasmid DNA, and the like. In another specific aspect, RNA may be any form of RNA, including RNAi, siRNA, snRNA, mRNA, tRNA, rRNA, microRNA, and hybrid sequences or synthetic or semi-synthetic sequences thereof.

The manipulation of molecular material according to aspects of the present invention may be useful in a variety of situations and environments. For example, the transfer of such material may be utilized to transfer molecular material into a single cell. Although any single cell would be considered to be within the present scope, in one specific aspect the single cell may be an oocyte. Other non-limiting examples of single cells include neuronal cells, fibroblasts, cancer cells, and the like. Additionally, it is also contemplated that molecular material may be transferred to particular regions or biological structures within a single cell. In one specific example, molecular material may be transferred into the nucleus of a single cell.

A variety of motions are contemplated to move the needle structure and the associated molecular material from the first locus to the second locus. In one aspect, for example, the needle structure can be moved along a linear or substantially linear path from the first locus to the second locus. One example of such a motion would include situations where the first locus and the second locus are substantially aligned with an elongate axis of the needle structure, with the first locus at or near the tip of the needle structure. By moving the needle structure forward along the elongate axis, the tip of the needle will move along a linear path from the first locus to the second locus. Alternatively, in other aspects the needle structure may also be moved in an additional direction that is out of the linear path of the needle structure. In such cases, however, it may be beneficial to maintain the orientation of the needle structure, particularly in those aspects where molecular material is being transferred into a cell. If such an orientation is not maintained, there may be a risk of damage to the cell being injected. More specifically, if a loci axis is defined between the first locus and the second locus, the angular relationship between the elongate axis of the needle structure and the loci axis should remain constant as the needle structure and the first locus are moved relative to one another. As such, in situations where the needle structure is moved in a direction away from the loci axis, the orientation of the needle structure would still be maintained parallel to the elongate axis established prior to movement. In another aspect, the angular relationship between the loci axis and the elongate axis need not remain constant, provided the needle structure be positioned so as the second loci is approached in a direction that is along the elongate axis. In other words, the needle structure may be moved to an intermediate locus, and movement of the needle structure from the intermediate locus to the second locus can be in a direction along the elongate axis of the needle structure at the intermediate locus.

Upon arrival of the needle structure at the second locus, the molecular material can be released. This can be accomplished in a variety of ways, and any method that releases the molecular material should be considered to be within the scope of the present invention. In one aspect, the charge of the needle structure can simply be released, thus allowing the molecular material to diffuse away at the second locus. It should be noted that the needle structure may not necessarily be completely discharged, but in some cases could be discharged to a degree sufficient to substantially release the charged molecular material associated with the needle structure. In another aspect, discharging the needle structure can include reversing the polarity of the needle structure charge. By utilizing this method, the molecular material may be actively driven from the needle structure, thus minimizing the amount of time the needle structure is present at the second locus.

The present invention additionally provides systems for manipulating molecular material. In one aspect for example, a system for manipulating molecular material can include a needle structure, a charging system electrically coupled to the needle structure, the charging system being operable to charge and discharge the needle structure, and a movement system operable to move the needle structure from a first locus to a second locus. In one specific aspect, the system may further include a charged molecular material sample associated with the needle structure. As has previously been described, such molecular material may include any molecular material sample that is purposefully attracted to or associated with the needle structure. Non-limiting examples of such samples include DNA, RNA, peptides, polymers, organic molecules, inorganic molecules, ions, and combinations thereof. A more specific list of non-limiting examples may include DNA, RNA, peptides, and combinations thereof.

In another specific aspect, the system can further include a single cell positioned to receive the needle structure upon operation of the movement system. Although a variety of single cells are contemplated, in one aspect the single cell is an oocyte.

Numerous needle structure configurations and materials are contemplated, and it should be noted that any material and configuration that allows the manipulation of molecular material through electrical charge and discharge should be considered to be within the present scope. In one aspect, for example, the material of the needle structure may include a metal or metal alloy, a conductive glass, a polymeric material, a semiconductor material, and combinations thereof. Non-limiting examples of metals for use in the needle structure include indium, gold, platinum, silver, copper, associated alloys, palladium, tungsten, aluminum, titanium, and combinations thereof. Polymeric materials that can be used to construct the needle structure can include any conductive polymer, non-limiting examples of which include polypyrrole doped with dodecyl benzene sulfonate ions, SU-8 polymer with embedded metallic particles, and combinations thereof. Non-limiting examples of useful semiconductor materials can include monocrystalline silicon, polycrystalline silicon, germanium, gallium arsenide, indium-tin oxide, and combinations thereof. It should additionally be noted that in some aspects the conductive material may be a conductive layer that is coated on a second material, where the second material provides the physical structure of the needle structure. Additionally, the needle structure may be comprised of a hollow, non-conductive material, such as a glass, where the hollow material is filled with a conductive material such as a conductive liquid. The needle structure may be of a variety of sizes depending on the intended use of the device. In one aspect, however, the tip of the needle structure may be less than about 5 microns across. In another aspect, the tip of the needle structure may be less than about 1 microns across. In yet another aspect, the tip of the needle structure may be less than about 100 nanometers across.

The charging system operatively coupled to the needle structure may include any system capable of electrically charging, maintaining the charge, and subsequently discharging the device. Non-limiting examples can include batteries, DC power supplies, photovoltaic cells, static electricity generators, capacitors, and the like. The charging system can include a switch for activation and deactivation, and in some aspects can also include a polarity switch to reverse polarity of the charge on the needle structure. In one aspect the system may additionally include multiple charging systems, one system for charging the needle structure with a charge, and another charging system for charging the needle structure with an opposite polarity charge. In one example scenario, an initially uncharged needle structure is brought into contact with a sample of a charged molecular material. The molecular material may be in water, saline, or any other liquid useful for molecular material manipulation. A charge opposite in polarity to the charge of the charged molecular material is applied to the needle structure, thus attracting a portion of the sample of molecular material thereto. The needle structure is then moved from the first locus to the second locus while the molecular material is held in place by the charge. Once at the second locus, the polarity of the charge at the needle structure can be reversed, thus releasing the molecular material from the needle structure, and in some cases actively driving the molecular material into the region surrounding the second locus. The needle structure can subsequently be withdrawn from the second locus.

A variety of movement systems are contemplated to move the needle structure from the first locus to the second locus. Any technique capable of moving the needle structure with sufficient precision to allow the manipulation of molecular material is considered to be within the present scope. Non-limiting examples of movement systems include, mechanical systems, magnetic systems, piezoelectric systems, electrostatic systems, thermo-mechanical systems, pneumatic systems, hydraulic systems, and the like. The needle structure may also be moved manually by a user. For example, a user may push the needle structure along a track from the first locus to the second locus. Additional movement systems are described more fully below.

In another aspect of the present invention, a system for manipulating molecular material is provided including a moveable support frame, a needle structure associated with the moveable support frame, the needle structure operable to carry molecular material therewith, where the moveable support frame is operable to move the needle structure from an initial position to an extended position, and wherein an elongate axis of the needle structure is maintained in a substantially constant orientation as the moveable support frame moves the needle structure from the initial position to the extended position. In a more specific aspect, a vertical elevation of the needle structure in the extended position is different from a vertical elevation of the needle structure in the initial position. In such a case, the elongate axis of the needle structure in the extended position is parallel to or substantially parallel to the elongate axis of the needle structure in the initial position. Furthermore, the system can include a charging system as described above. It should be noted that the term "vertical" as has been used herein refers to movement relative to the elongate axis of the needle structure in the initial position.

Figure 1:
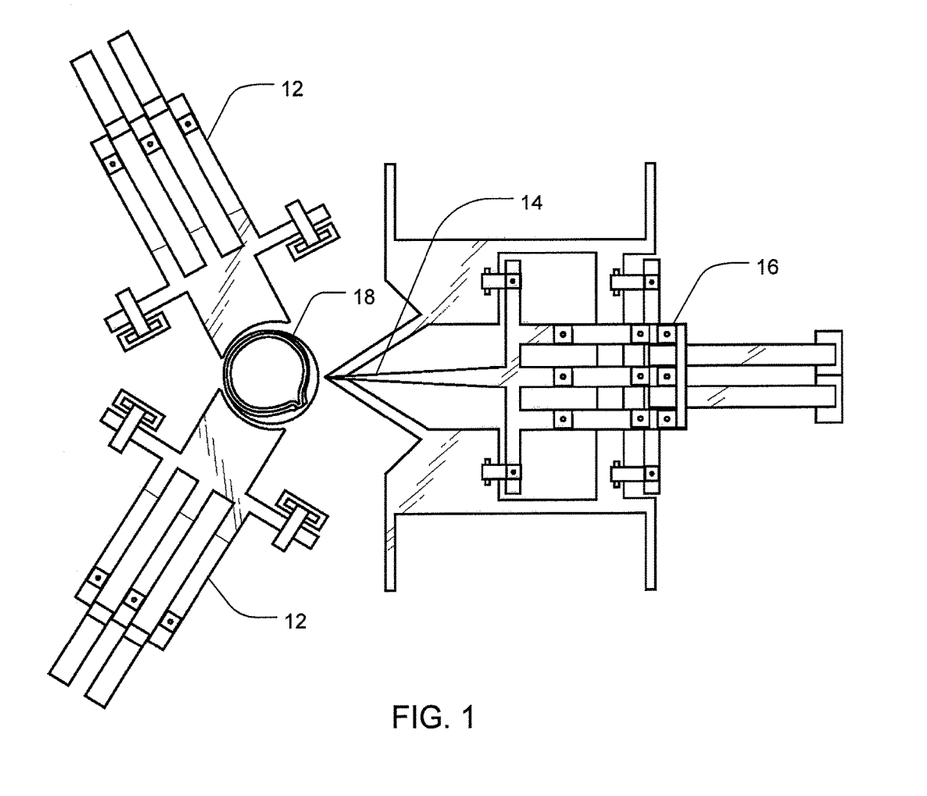
FIG. 1 is a view of a molecular material manipulation system in accordance with one embodiment of the present invention.

Additional components of the system are contemplated, depending on the nature of the molecular material manipulation. For example, a system that is utilized to transfer a molecular material such as DNA to the nucleus of a single cell can include a support structure positioned adjacent to the moveable support frame, where the support structure is operable to secure a single cell in a position to receive the needle structure when in the extended position. One example of a system having such a support structure for holding an oocyte is shown in FIG. 1. A pair of oocyte supports 12 are used to hold the oocyte 18 in a position to receive the needle structure 14 when moved into the extended position by the moveable support frame 16. In this aspect the center of the oocyte 18 is located such that the nucleus of the oocyte is aligned with the needle structure when it is brought to the extended position. In another aspect, an oocyte may be placed in a recess in the substrate holding the moveable support frame such that the approximate center of the oocyte is aligned with the elongate axis of the needle structure when in the initial position (not shown). The extended position in this configuration can thus be achieved by moving the needle structure along the elongate axis toward the oocyte. Additional configurations for support structures would be readily apparent to one of ordinary skill in the art once in possession of the present disclosure, and such configurations are considered to be within the present scope.

In yet another aspect of the present invention, a system for manipulating molecular material can include a moveable support frame, a needle structure associated with the moveable support frame, the needle structure being chargeable between a first charged state and a second charged state, the moveable support frame being operable to move the needle structure from an initial position to an extended position, wherein an elongate axis of the needle structure is maintained in a substantially constant orientation as the moveable support frame moves the needle structure from the initial position to the extended position. Furthermore, in one specific aspect a vertical elevation of the needle structure in the extended position is different from a vertical elevation of the needle structure in the initial position.

As has been described, a variety of configurations are contemplated for manipulating molecular material according to aspects of the present invention. In one specific example, a pumpless microelectromechanical system (MEMS) device is provided for the introduction of foreign molecular material into a single cell. Due to the small size of such devices, it may be beneficial to create a system that is at least substantially self-contained. The use of the molecular material manipulation techniques of the present invention eliminates the need for precise injection pumps, thus facilitating such a self-contained system.

In order to inject foreign molecular material into a single cell such as an oocyte, the system should effectively constrain the cell and introduce foreign molecular material into the cell's nucleus. As was shown in FIG. 1, the system may utilize three polysilicon arms arranged around the oocyte. Two of these arms (support structures 12) are arranged and configured to constrain the cell, while the third (moveable support frame 16) includes a needle structure for introducing molecular material into the cell. In one aspect, the three arms will cause the oocyte to align in a proper position as they come into contact. As has also been described, any of the three arms may be actuated manually by the user, or they may be actuated by motors or other movement systems.

Figure 2:
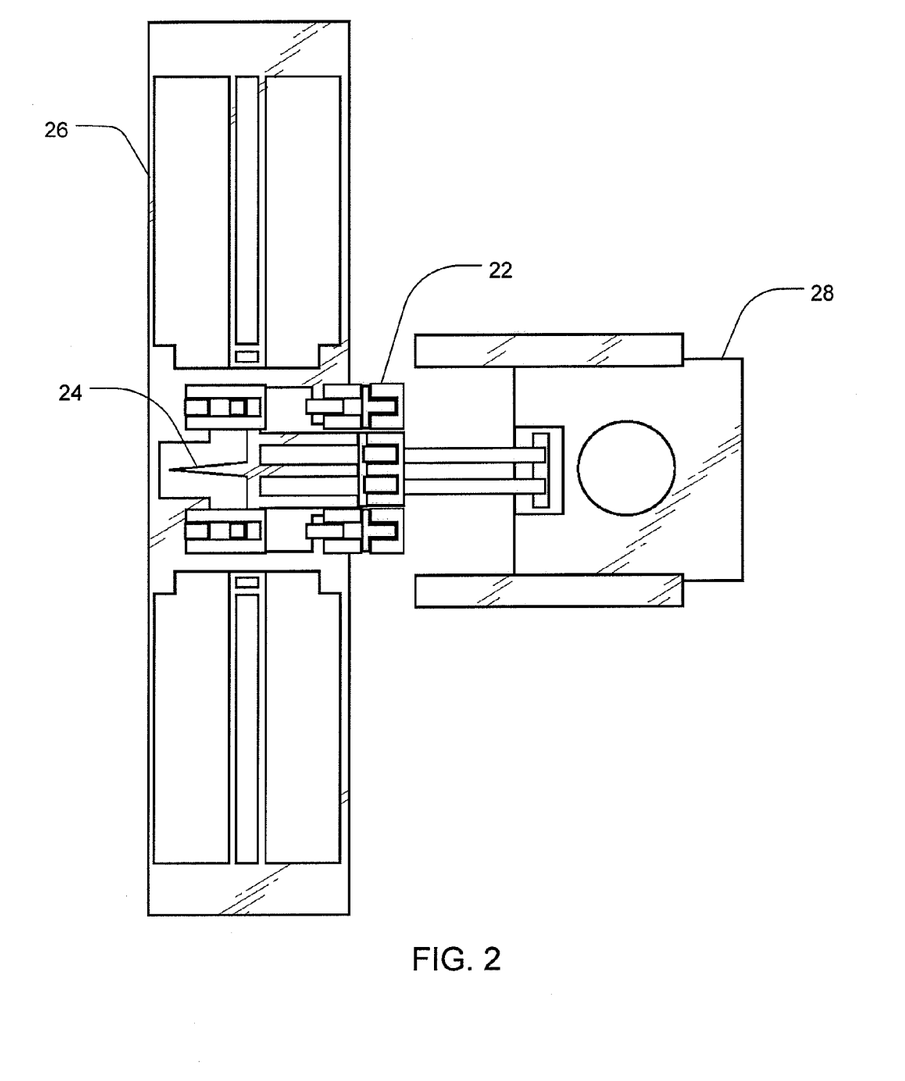
FIG. 2 is a view of a molecular material manipulation system in accordance with another embodiment of the present invention.

To hold an oocyte in place, the two support structure arms rise up out of plane and move toward the cell. The arms are lamina-emergent, change point, parallel-guiding, six-bar mechanisms, kinematically grounded to the chip substrate, and receive a linear input from a slider. The constraining arms are designed to contact the cell wall above the cell's midline to prevent both lateral and vertical displacements during transfer of molecular material. For oocytes such as mouse cells (80-100 μm in diameter), the constraining arms are designed to have a total vertical displacement of 68.2 μm and a total horizontal displacement of 84.6 μm from its fabricated position. Given such dimensions, one of ordinary skill in the art could readily modify the present system to be adaptable to other cell sizes. The constraining arm's large horizontal displacement thus allows for a larger area into which the cell can be initially placed. The needle arm, similar to the constraining arms, can be made of a lamina-emergent, change-point, parallel-guiding, six-bar mechanism receiving a linear input from a slider. However, the needle structure mechanism is attached to a moveable support frame. The moveable support frame is a fully compliant, parallel guiding mechanism with, for mouse oocytes, 50 μm of in-plane travel. In one aspect, the moveable support frame is sufficiently stiff so that as the slider moves forward, the needle rises up out of the plane with minimal horizontal displacement in the translating stage. Further forward movement causes the moveable support frame to deflect and move the needle structure horizontally in its extended position toward the second locus, thus maintaining a parallel relationship between the elongate axis of the needle structure in the initial position with the elongate axis in the extended position. The previously described system is shown more fully in FIGS. 2 and 3. FIG. 2 shows the system in the initial position, including the moveable support frame 22, the needle structure, 24, and a compliant folded beam suspension 26 to facilitate the horizontal movement of the needle structure 24 once in the extended position. The aspect shown in FIG. 2 additionally shows a manual slider 28 to allow a user to manually actuate the device from the initial position to the extended position. The system can additionally includes electrical contacts to charge the needle structure (not shown).

Figure 3:
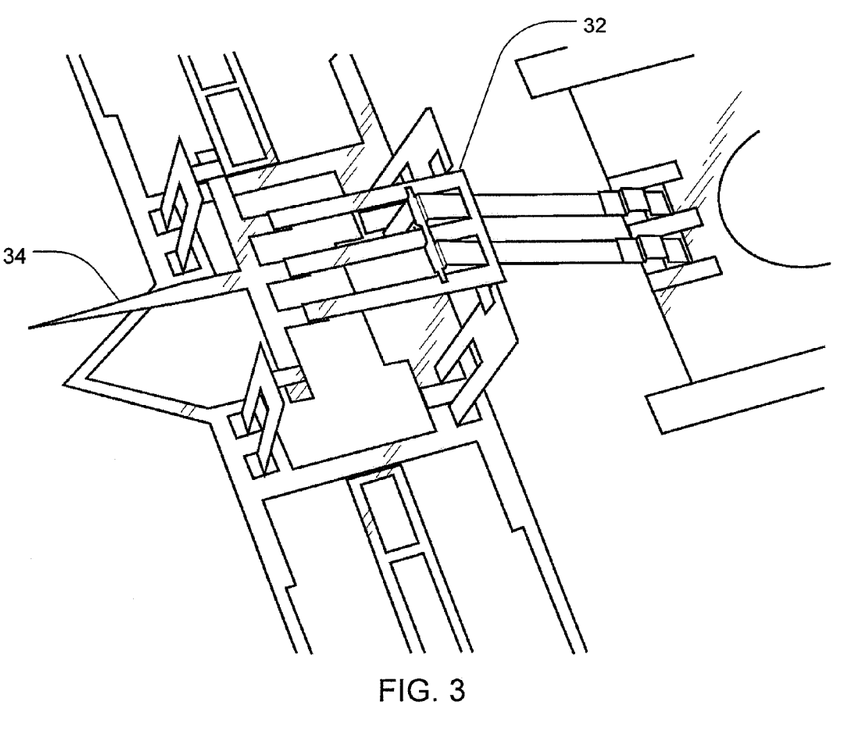
FIG. 3 is a view of a molecular material manipulation system in accordance with yet another embodiment of the present invention.

FIG. 3 shows the system in the extended position. Note that as the moveable support frame 32 is moved from the initial position shown in FIG. 2, the needle structure 34 is maintained in an orientation that is parallel to the needle structure in the initial position.

The following description relates to DNA, however the present scope should not be limited to such. Rather, DNA is used to describe various embodiments for convenience. Though it has a net charge of zero, DNA has an unequal distribution of internal charges resulting in a negative character equal to two electrons for every base pair. Exploiting the electrical characteristics of DNA, the needle structure may be designed to attract, associate, and release molecular material using static electric charges. Thus, the needle requires no pumps, no capillaries, and consists only of an easily fabricated, solid, pointed body. The needle and the bottommost monosilicon layer of a MEMS chip may form a capacitor. Voltage is applied to the needle structure using a compliant beam attached to either side the moveable support frame. The compliant beam may be highly folded and attach to the needle structure about halfway between the two vertical legs to prevent the generation of moments that might cause the needle structure to rotate about a horizontal axis.

The compliant beams are electrically coupled to fixed electrical bonding pads near the device through which charge can be applied. In this case, a positive charge would be applied to attract the negatively charged DNA molecules. The negative terminal of the voltage supply can be attached to a bonding pad connected to the underlying monosilicon substrate.

The MEMS construction can be achieved by a variety of methods. The MEMS methods themselves are well known, and will not be discussed in detail. One exemplary process, however, is polyMUMPs (Polysilicon MEMS Multi-User Processes), a fabrication process for surface micromachined polysilicon structures (MEMSCAP USA).

Figure 4:
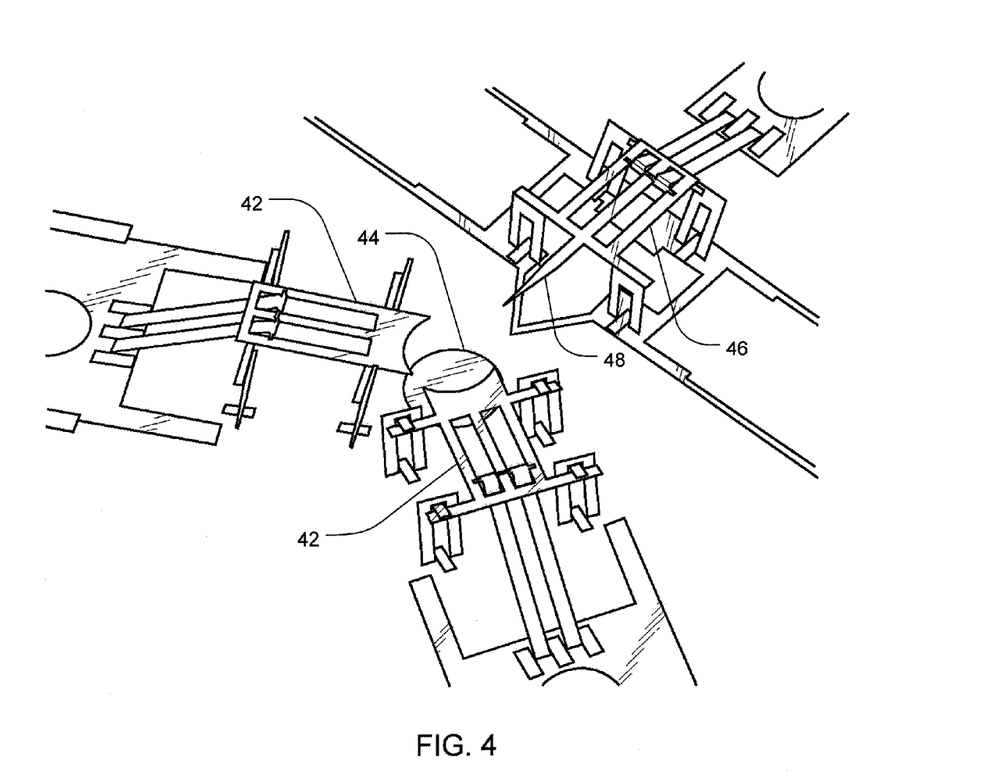
FIG. 4 is a view of a molecular material manipulation system in accordance with a further embodiment of the present invention.

Accordingly, the MEMS system described can be operated as follows: DNA is introduced into the solution containing the needle structure. A positive charge is applied to the needle structure to attract the DNA sample. A single cell such as an oocyte is positioned at a point to receive the needle structure and the associated DNA. As is shown in FIG. 4, constraining structures 42 are raised to align and constrain the oocyte. In FIG. 4, the oocyte would be located on top of the pad shown at 44. The moveable support frame 46 is raised to the extended position, and the needle structure 48 is extended horizontally forward into the oocyte until the nucleus has been punctured by the needle. The polarity of the electrical charge can then be reversed to release the DNA into the oocyte nucleus, and the needle structure can be retracted from the cell.

In one aspect, to be useful a practical, self-contained pumpless MEMS injection device should satisfy three principle constraints. First, to be practically useful, the MEMS device should must concentrate measurable amounts of DNA on its surface in a reasonably short amount of time. Second, to increase the likelihood of cell survival, the MEMS needle structure should remain inside the cell for as little time as possible; e.g. the MEMS needle structure should be capable of repelling DNA concentrated on its surface in a matter of seconds. Third, to prevent damage to the device or the cell, and to prevent unwanted bubble formation, the MEMS needle structure should not cause electrolysis of the surrounding water. In some cases, not causing electrolysis of the water surrounding the MEMS needle structure, may be particularly limiting. In initial feasibility testing, electrolysis occurred at approximately 1.8 V on gold bond pads submerged in an aqueous solution of 0.9% NaCl (i.e. saline solution). In initial testing, when electrolysis was allowed to occur, delamination of gold-on-polysilicon bond pads, and near complete removal of gold from gold on polysilicon bond pads were observed. Thus, it appears that for some applications the operating voltage for the MEMS needle structure should be less than 1.8 V.

EXAMPLES

The following examples are provided to promote a more clear understanding of certain embodiments of the present invention, and are in no way meant as a limitation thereon.

Example 1

DNA Visualization and Imaging Methods

4',6-diamidino-2-phenylindole dihydrochloride (DAPI) is used to visualize the DNA in the following example. DAPI exhibits low toxicity and its strong fluorescence under ultra-violet illumination. When dissolved in water and not bound to DNA, DAPI has an excitation maximum of 355 nm (ultra-violet light) and an emission maximum of 453 nm (blue light). When DAPI is bound to DNA its excitation maximum changes to 388 nm and its emission maximum shifts to 454 nm, and the intensity of the emitted light increases roughly twenty-fold compared to free DAPI. The increase in emission intensity when DAPI binds with DNA makes it possible to distinguish between unbound DAPI and DAPI-stained DNA.

Figure 5:
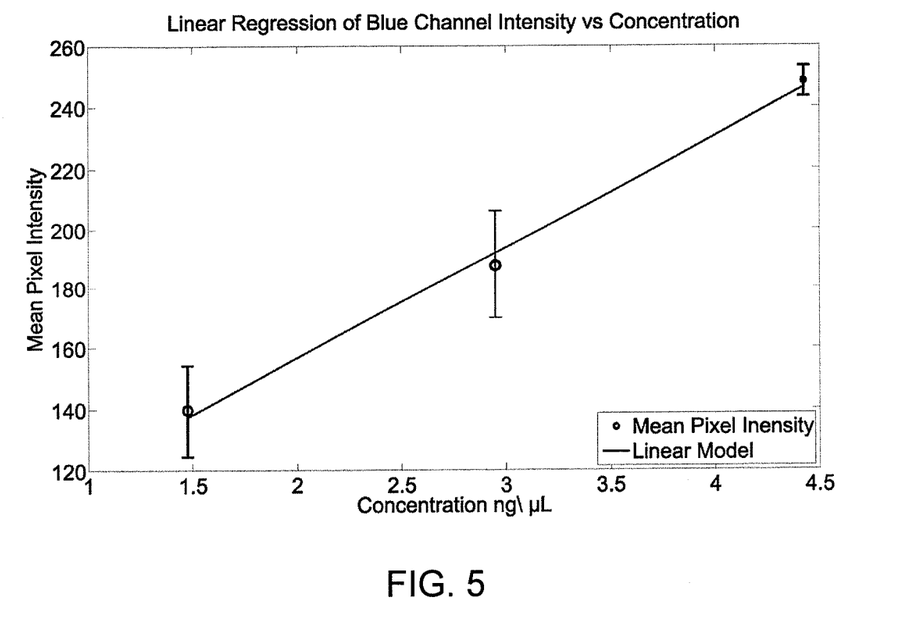
FIG. 5 is graphical plot of DNA concentration to pixel intensity in accordance with yet a further embodiment of the present invention.

DAPI-stained DNA is visualized using a Zeiss Axioskop Fluorescence Microscope with UV illumination and a purpose-built blue light filter for imaging DAPI stained samples. Because the DAPI-DNA complex fluoresces in the blue portion of the visible spectrum, the blue color channel is isolated from raw RGB images to simplify image analysis. To provide quantitative estimates of the concentration of DNA on or near the needle structure, a regression model is made of blue pixel intensity (I) as a function of DNA concentration (C). DAPI stained DNA samples of known and uniform concentration are imaged using the aforementioned parameters, and the mean blue channel pixel intensities of the images are calculated using a MATLAB script. The relationship between concentration in ng/μL and blue pixel intensity is linear as shown in FIG. 5. A linear fit to the data gives the relationship shown in Equation I $$C=(I-83.07)/36.788 \qquad \text{I}$$

The blue channel intensity measurements are shown with 95% error bounds, and the linear model of the data given in Equation I is represented by the solid line. Because of the long exposure used (six seconds), the intercept value (blue pixel intensity at 0 ng/μL) is highly susceptible to changes in ambient lighting conditions. In cases where the ambient lighting conditions cause the intercept to deviate from the value of 83.07 shown in Equation I, a reference image of a MEMS die submerged in the appropriate media (either distilled water or 0.9% NaCl) with no DNA present can be used to calculate the value of the intercept under those lighting conditions.

Example 2

DNA Attraction Experiment

The DNA attraction and repulsion experiments are performed both in distilled water and in 0.9% saline solution. In both cases, the experiments follow identical protocols, with the exception of the media into which the device is submerged. A MEMS device as has been described herein is covered in approximately 2 mm of either distilled water or 0.9% saline solution. A 1-2 μL drop of 306 ng/μL DAPI stained DNA is placed in the solution near the device using a calibrated pipette. The needle structure of the MEMS device is connected to the positive terminal of a voltage source providing 1.5 V DC. The substrate of the MEMS device is connected to the negative terminal of the voltage source. Images can be taken to verify the DAPI-stained DNA on the surface of the needle structure. Approximate concentrations of the DNA can be calculated using the linear model of Equation I.

Example 3

DNA Repulsion Experiment

DNA is attracted to the tip of a MEMS needle structure as is described in Example 2, by connecting the needle structure to the positive terminal of a 1.5 V DC voltage source and connecting the MEMS device substrate to the negative terminal of the voltage source. Following attraction of DNA, the polarity of the electrical charge is then reversed so that the positive terminal is connected to the MEMS device substrate and the negative terminal is connected to the needle structure. Images can be taken from the time the polarity is reversed to verify DNA release and repulsion. Additionally, the time between connecting the MEMS needle structure to the negative terminal and when DNA is clearly repelled from the needle structure can be calculated, and approximate concentrations can be calculated using the linear model given in Equation I.

Example 4

Distilled Water Experiment

A MEMS device as has been described herein is covered in approximately 2 mm of distilled water. A 1-2 µL drop of 306 ng/µL DAPI stained DNA is placed in the distilled water near the device using a calibrated pipette. The needle structure of the MEMS device is connected to the positive terminal of a voltage source providing 1.5 V DC. The substrate of the MEMS device is connected to the negative terminal of the voltage source. Images can be taken to verify the DAPI-stained DNA on the surface of the needle structure. After 1 hour 17 minutes of incubation, approximately 2.4-2.5 ng/µL is attracted to the tip of the charged needle structure. The approximations are derived from the linear model of Equation I.

Following attraction of DNA, the polarity of the electrical charge is then reversed so that the positive terminal is connected to the MEMS device substrate and the negative terminal is connected to the needle structure. The negatively charged needle structure repels measurable amounts of DNA from its tip within six seconds of the polarity change.

Example 5

0.9% Saline Solution Experiment

A MEMS device as has been described herein is covered in approximately 2 mm of 0.9% saline solution. A 1-2 µL drop of 306 ng/µL DAPI stained DNA is placed in the saline solution near the device using a calibrated pipette. The needle structure of the MEMS device is connected to the positive terminal of a voltage source providing 1.5 V DC. The substrate of the MEMS device is connected to the negative terminal of the voltage source. When connected in this manner and submerged in 0.9% NaCl solution, the MEMS needle structure has a capacitance of approximately 230 pf. Images can be taken to verify the DAPI-stained DNA on the surface of the needle structure. After 5 minutes 46 seconds of incubation, approximately 2.2-2.4 ng/µL is attracted to the tip of the charged needle structure. The approximations are derived from the linear model of Equation I.

Following attraction of DNA, the polarity of the electrical charge is then reversed so that the positive terminal is connected to the MEMS device substrate and the negative terminal is connected to the needle structure. The negatively charged needle structure repels measurable amounts of DNA from its tip within six seconds of the polarity change.

It is to be understood that the above-described compositions and modes of application are only illustrative of preferred embodiments of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A method for delivering a charged molecular material sample into a cell, comprising:
    obtaining an elongate needle structure tapering at one end to a tip, wherein at least a portion of the tip includes a conductive material configured to receive a positive charge;
    applying a positive charge to the conductive material at the tip;
    associating the charged molecular material sample to the tip via the positive charge at a first locus outside of the cell;
    moving the tip of the elongate needle structure from the first locus outside of the cell to a second locus inside the cell, said movement being along an elongate axis of the elongate needle structure in a plane that maintains an angular relationship parallel to a surface upon which the cell rests;
    applying a negative charge to the conductive material at the tip in order to release the charged molecular material sample at the second locus inside the cell; and
    withdrawing the tip from the cell.

2. The method of claim 1, wherein the charged molecular material sample is a genetic substance with a phosphate backbone.

3. The method of claim 1, wherein moving the tip of the elongate needle structure into the cell further includes moving the tip of the needle structure into a particular biological structure within the cell.

4. The method of claim 3, wherein the particular biological structure is a cell nucleus.

5. The method of claim 1, wherein the positive charge has a voltage of less than 1.8 V.

6. The method of claim 1, wherein the positive charge has a voltage of 1.5 V.

7. A method for delivering a charged molecular material sample into a cell, comprising:
    obtaining an elongate pump-less needle structure tapering at one end to a tip, wherein at least a portion of the tip includes a conductive material configured to receive a positive charge;
    applying a positive charge to the conductive material at the tip;
    associating the charged molecular material sample to the tip via the positive charge at a first locus outside of the cell;
    moving the tip of the elongate pump-less needle structure from the first locus outside of the cell to a second locus inside the cell, said movement being along an elongate axis of the elongate pump-less needle structure in a plane that is parallel to a surface upon which the cell rests;
    applying a negative charge to the conductive material at the tip in order to release the charged molecular material sample at the second locus inside the cell; and
    withdrawing the tip from the cell.

* * * * *